(12) United States Patent
Diver

(10) Patent No.: US 9,212,327 B2
(45) Date of Patent: Dec. 15, 2015

(54) SYSTEM AND PROCESS FOR PRODUCING FUEL WITH A METHANE THERMOCHEMICAL CYCLE

(71) Applicant: ADVANCED COOLING TECHNOLOGIES, INC., Lancaster, PA (US)

(72) Inventor: Richard B. Diver, Albuquerque, NM (US)

(73) Assignee: Advanced Cooling Technologies, Inc., Lancaster, PA (US)

( * ) Notice: Subject to any disclaimer, the term of this patent is extended or adjusted under 35 U.S.C. 154(b) by 0 days.

(21) Appl. No.: 14/445,492

(22) Filed: Jul. 29, 2014

(65) Prior Publication Data

US 2015/0038600 A1    Feb. 5, 2015

Related U.S. Application Data

(60) Provisional application No. 61/859,811, filed on Jul. 30, 2013.

(51) Int. Cl.
| | |
|---|---|
| *C10J 1/20* | (2006.01) |
| *C10L 3/08* | (2006.01) |
| *C07C 29/151* | (2006.01) |

(52) U.S. Cl.
CPC ............... *C10J 1/20* (2013.01); *C07C 29/1518* (2013.01); *C10L 3/08* (2013.01)

(58) Field of Classification Search
CPC ........... C10J 1/20; C07C 29/1518; C10L 3/08
See application file for complete search history.

(56) References Cited

U.S. PATENT DOCUMENTS 3,984,530 A * 10/1976 Dreyfuss et al. .............. 423/650
4,756,806 A *  7/1988 Krist et al. .................... 205/462

OTHER PUBLICATIONS

Brown, L.C., Besenbruch, G.E., Lentsch, R.D., Schultz, K.R., Funk, J.F., Pickard, P.S., Marshall, A.C., Showalter, S.K., 2003 "High Efficiency Generation of Hydrogen Fuels Using Nuclear Power," GA-A24285. Prepared under the Nuclear Energy Research Initiative Program for the US Department of Energy, General Atomics, San Diego, CA.

McQuillan, B.W., Brown, L.C., Besenbruch, G.E., Tolman, R., Cramer, T., Russ, B.E., Vermillion, B.A., Earl, B., Hsieh, T., Chen, Y., Kwan, K., Diver, R., Siegal, N., Weimer, A., Perkins, C., and Lewandowski, A., 2010, "High Efficiency Generation of Hydrogen Fuels Using Solar Thermal-Chemical Splitting of Water (Solar Thermo-Chemical Splitting for H2)," GA-A24972. Prepared under Solar Thermochemical Hydrogen Grant No. DE-FG36-03G013062 for the US Department of Energy and F03-STCH2-002 for the University of Nevada Las Vegas Research Foundation, General Atomics, San Diego, CA.

Onuki, K., Shimizu, S., Nakajima, H., Ikezoe, Y., Sato, S., 1987, "Study of Catalytic Reduction of Methanol for Methane-Methanol Thermochemical Hydrogen Production Cycles," Int. J. Hydrogen Energy, vol. 12, No. 8 pp. 555-559.

Stephane Abanades, Patrice Charvin, Gilles Flamant, Pierre Neveu, 2006, "Screening of Water-Splitting Thermochemical Cycles Potentially Attractive for Hydrogen Production by Concentrated Solar Energy", Energy vol. 31(14) pp. 2805-2822.

* cited by examiner

*Primary Examiner* — Sudhakar Katakam
(74) *Attorney, Agent, or Firm* — McNees Wallace & Nurick LLC

(57) ABSTRACT

A thermochemical process and system for producing fuel are provided. The thermochemical process includes reducing an oxygenated-hydrocarbon to form an alkane and using the alkane in a reforming reaction as a reducing agent for water, a reducing agent for carbon dioxide, or a combination thereof. Another thermochemical process includes reducing a metal oxide to form a reduced metal oxide, reducing an oxygenated-hydrocarbon with the reduced metal oxide to form an alkane, and using the alkane in a reforming reaction as a reducing agent for water, a reducing agent for carbon dioxide, or a combination thereof. The system includes a reformer configured to perform a thermochemical process.

18 Claims, 1 Drawing Sheet

SYSTEM AND PROCESS FOR PRODUCING FUEL WITH A METHANE THERMOCHEMICAL CYCLE

PRIORITY

The present disclosure claims priority and benefit of U.S. Provisional Patent Application No. 61/859,811, titled "SYSTEM AND PROCESS FOR PRODUCING FUEL WITH A METHANE THERMOCHEMICAL CYCLE" and filed Jul. 30, 2013, the entirety of which is incorporated by reference.

STATEMENT CONCERNING FEDERALLY-SPONSORED RESEARCH

The present invention was made in connection with Government support under contract number DE-SC0004729 awarded by the Department of Energy. The Government may have certain rights with the invention.

FIELD OF THE INVENTION

The present invention is directed to processes and systems for producing fuel by using a methane thermochemical cycle. More specifically, the present invention relates to chemically reducing an oxygenated-hydrocarbon that is used to then promote the splitting of water and/or carbon dioxide, producing fuel. The oxygenated hydrocarbon is regenerated and completes the thermochemical cycle.

BACKGROUND OF THE INVENTION

Most of the energy consumed in the world today is "stored solar energy" in the form of fossil fuels, such as petroleum, natural gas, and coal. Fossil fuels, however, are finite and their combustion has been tied to an increase in the amount of carbon dioxide in the atmosphere and other pollutants in the environment. Their limited availability also has national security and economic implications.

Solar and nuclear energy are not limited in the same manner as fossil fuels. They can provide viable long-term persistent energy options and be an environmentally advantageous, long-term alternative to fossil fuels. Such sources can produce hydrogen from water, which can be used as an independent, clean-burning fuel.

Thermochemical processes for converting solar or nuclear energy into fuels are potentially more straightforward, efficient, and less costly than using electric power to electrolyze water. Thermochemical cycles utilize high-temperature heat and a series of chemical reactions to produce fuels. Thermochemical water-splitting cycles utilize a series of chemical reactions with the overall reaction $H_2O \rightarrow H_2 + \frac{1}{2}O_2$. Thermochemical carbon dioxide-splitting cycles utilize a similar series of chemical reactions with the overall reaction $CO_2 \rightarrow CO + \frac{1}{2}O_2$. All of the other chemicals are recycled within the process.

Recent solar thermochemical research has focused on two-step metal oxide cycles that alternately thermally reduce a metal oxide, such as magnetite ($Fe_3O_4$) to wustite (FeO), producing oxygen, and then oxidize the metal oxide with water or carbon dioxide to produce hydrogen or carbon monoxide, respectively. The metal oxide is typically cycled between the high temperature thermal reduction step and a lower temperature re-oxidation step. For example, cerium oxide is a metal oxide that has received notable attention. The metal oxide cycles are attractive in that they involve only two chemical steps. However, they require temperatures of at least 1400° C. for reasonable efficiencies, even with the addition of other dopants to the metal oxides to lower the required thermal reduction temperature. These high temperatures preclude the use of nuclear power and severely impact the design and efficiency of solar collection hardware.

To split water or carbon dioxide at lower temperatures, known nuclear driven thermochemical cycle work has centered on cycles that involve the decomposition of sulfuric acid, with the sulfur-iodine and hybrid sulfur processes receiving significant attention. A number of thermochemical cycles have been proposed; however, they rely upon sulfur oxides or other corrosive or hazardous materials, require substantial amounts of electrical power, have failed to be operational, produce corrosive and/or toxic chemicals, are harmful to the environment, create safety concerns, or a combination thereof.

A system and process for producing fuel with a methane thermochemical cycle that do not suffer from one or more of the above drawbacks would be desirable in the art.

BRIEF DESCRIPTION OF THE INVENTION

In an embodiment, a thermochemical process includes reducing an oxygenated-hydrocarbon to form an alkane and using the alkane in a reforming reaction as a reducing agent for water, a reducing agent for carbon dioxide, or a combination thereof.

In another embodiment, a thermochemical process includes reducing a metal oxide to form a reduced metal oxide, reducing an oxygenated-hydrocarbon with the reduced metal oxide to form an alkane, and using the alkane in a reforming reaction as a reducing agent for water, a reducing agent for carbon dioxide, or a combination thereof.

In another embodiment, a system includes a reformer configured to perform a thermochemical process. The thermochemical process includes reducing an oxygenated hydrocarbon to form an alkane and using the alkane in a reforming reaction as a reducing agent for water, a reducing agent for carbon dioxide, or a combination thereof.

Other features and advantages of the present invention will be apparent from the following more detailed description of the preferred embodiment, taken in conjunction with the accompanying drawings which illustrate, by way of example, the principles of the invention.

DETAILED DESCRIPTION OF THE INVENTION

Provided is a system and process for producing fuel with a methane cycle. Embodiments of the present disclosure, for example, in comparison to processes and systems not including one or more of the features disclosed herein, permit operation that is devoid of one or more undesirable intermediates (for example, being devoid of or substantially devoid of $SO_2$, metal sulfate, dopants, catalysts, or combinations thereof), permit solar flux to directly illuminate a metal oxide, permit water and/or carbon dioxide to be split, permit fuel to be produced (for example, hydrogen, carbon monoxide, or a combination thereof, or even methanol in one variant of the process), or a combination thereof.

Figure 1:
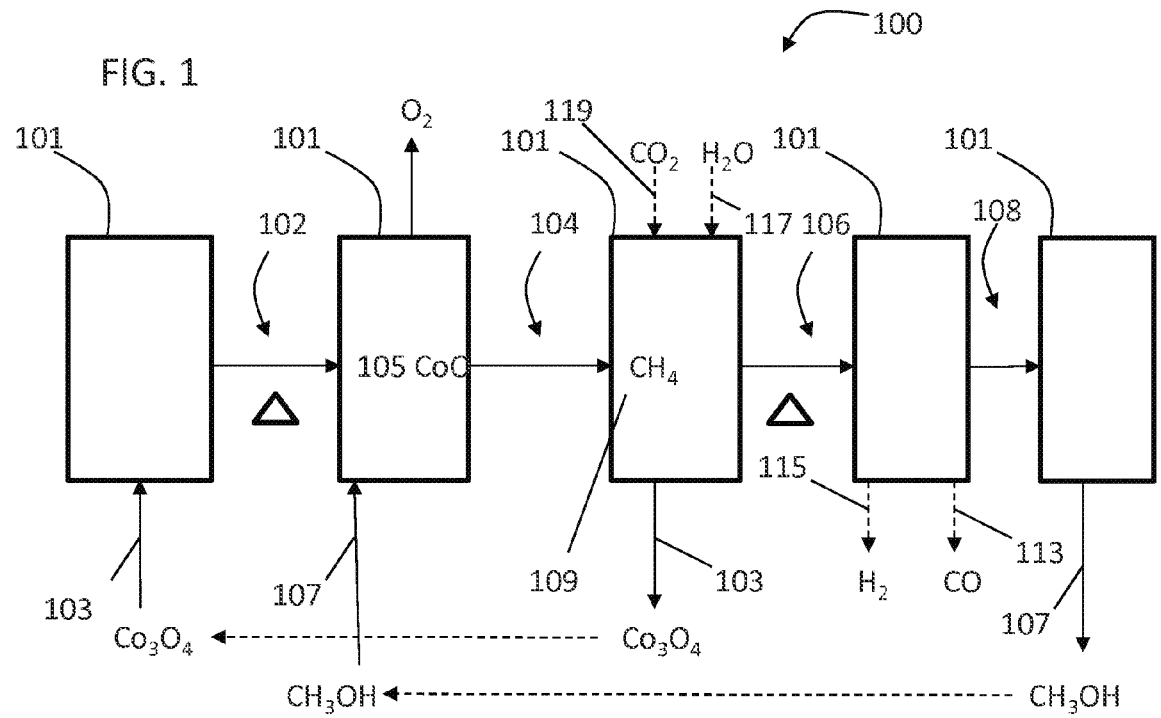
FIG. 1 schematically depicts an embodiment of a system performing an embodiment of a four-step process, according to the disclosure.
Figure 2:
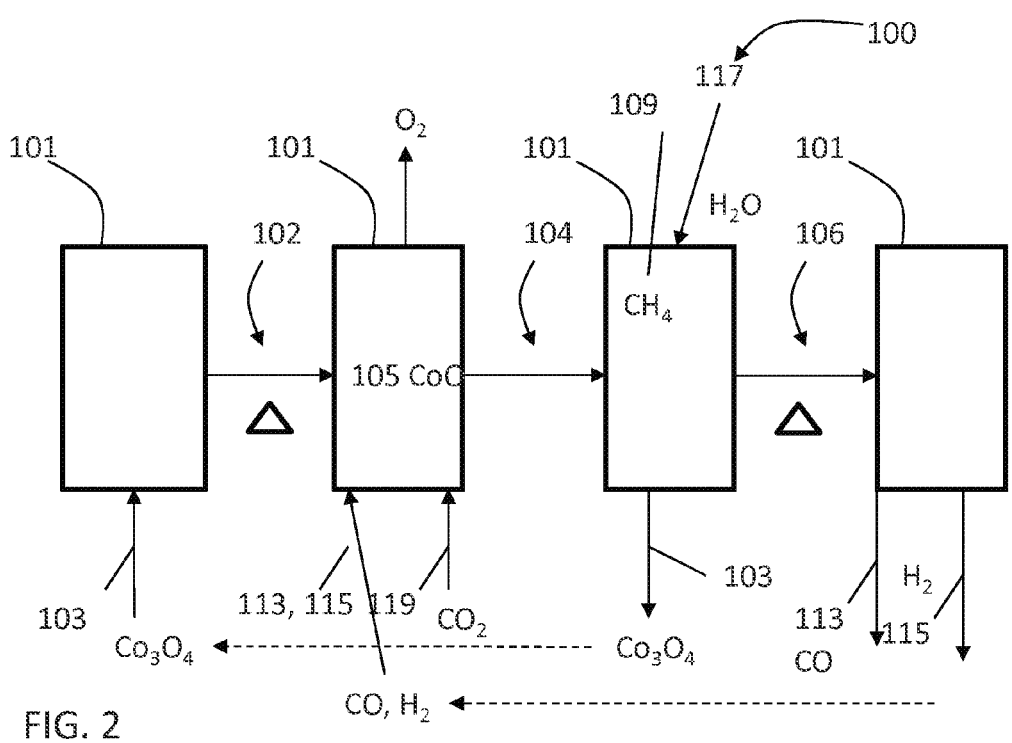
FIG. 2 schematically depicts an embodiment of a system performing an embodiment of a three-step process, according to the disclosure.

Referring to FIGS. 1 and 2, a process 100, according to the disclosure, is a four-step process (see FIG. 1) or a three-step process (see FIG. 2) capable of producing fuel through use of a methane (or alkane) cycle. The thermochemical process 100 includes reducing, such as, thermally-reducing (step 102) with solar or nuclear heat, for example, a metal oxide 103 to form a thermally-reduced metal oxide 105 and reducing (step 104) an oxygenated-hydrocarbon 107 (for example, methanol, ethanol, butanol, propanol, any other suitable oxygenated-hydrocarbon, or a combination thereof, or syngas (mixture of CO 113 and H2 115) as in FIG. 2) with the thermally-reduced metal oxide 105 to form an alkane, such as methane 109, capable of being used as an intermediate reactant for further processing.

The thermochemical system 101 is configured for the thermochemical process 100. In one embodiment, the thermochemical system 101 produces fuel (for example, as $H_2$, CO, $CH_3OH$, or a combination thereof) from the thermochemical process 100 in conjunction with a persistent or substantially persistent energy source, such as a solar power system or a nuclear power system.

The thermally-reducing (step 102) and the reducing (step 104) are concurrent, substantially concurrent, or sequential. The thermally-reducing (step 102) and the reducing (step 104) produce a re-oxidized metal oxide 103. In contrast to other processes, the re-oxidized metal oxide 103 is not directly re-oxidized with water or carbon dioxide to produce hydrogen or carbon monoxide directly. Instead, the re-oxidized metal oxide 103 is produced by reducing the oxygenated-hydrocarbon 107 (as shown in FIG. 1) and/or syngas 115 (as shown in FIG. 2).

Although not intending to be bound by theory, in an embodiment with the oxygenated-hydrocarbon 107 being methanol, due to the oxygen binding energy of methanol, for example, being less than half that of the oxygen-hydrogen bond in water 117 or the oxygen-carbon monoxide bond in carbon dioxide 119, the metal oxide 103 is selected to be more readily thermally-reduced (step 102), for example, at temperatures less than otherwise required for a two-step process. The reduced metal oxide 105 splits $CH_3OH$ rather than $CO_2$ or $H_2O$ directly. In comparison, to thermally reduce cerium oxide ($2CeO_2 \rightarrow Ce_2O_3 + \frac{1}{2}O_2$) with products and reactants at their standard states requires temperatures in excess of 2300° C. Similarly, in reducing magnetite to wustite ($Fe_3O_4 \rightarrow 3FeO + \frac{1}{2}O_2$), temperatures in excess of 2700° C. are used. However, selecting cobalt oxide as the metal oxide 103, according to an embodiment of the present disclosure, for example, permits the metal oxide 103 to be reduced at temperatures of less than 1000° C. ($Co_3O_4 \rightarrow 3CoO + \frac{1}{2}O_2$) and the thermally-reduced metal oxide 105, being thermally-reduced cobalt oxide, is thermodynamically capable of being re-oxidized by methanol to produce the methane 109 at temperatures less than about 380° C. ($3CoO + CH_3OH \rightarrow CH_4 + Co_3O_4$).

In one embodiment, the metal oxide 103 is hematite/magnetite ($Fe_2O_3/Fe_3O_4$), having a methanol reduction reaction to the methane 109 that is thermodynamically more favorable than that of cobalt oxide; however, in this embodiment, the thermal reduction (step 102) requires temperatures in excess of 1360° C. in air. Other metal oxides are capable of being used to tailor thermodynamic and kinetic properties by using mixed oxides. When selecting the metal oxide 103 without consideration of being more readily thermally-reduced (step 102), for example, when selecting cerium oxide or magnetite, a higher extent of reduction is achieved by the use of a vacuum or sweeping with an inert or otherwise oxygen-free gas. Such measures decrease system-level efficiency and temperatures, however, a temperature of at least 1400° C. is still required thermodynamically. These higher temperatures for thermally-reducing (step 102) the metal oxide 103 result in significant materials issues and low solar efficiency. Also, advanced nuclear heat sources cannot provide these temperatures.

In one embodiment, the thermochemical process 100 includes producing carbon monoxide 113 and hydrogen 115 from the methane 109 and water 117 (known as steam reforming), methane 109 and carbon dioxide 119 (known as dry reforming), or a combination thereof. At least a portion of the methane 109 is reformed with water 117 and/or carbon dioxide 119 using heat, for example, from a solar power system and/or nuclear power system, to produce the carbon monoxide 113 and the hydrogen 115. Because reforming the methane 109 produces more moles of the hydrogen 115 or the carbon monoxide 113 compared to what is needed to synthesize the methanol used to generate the methane 109, the net reaction is the production of the hydrogen 115, carbon monoxide 113, or a product syngas, including the hydrogen 115 and the carbon monoxide 113. In one embodiment, the heating value of the product syngas is increased compared to the methane 109 (for example, by between 25% and 30%, when the water 117 and the carbon dioxide 119 are being reformed, respectively).

Referring specifically to FIG. 1, in one embodiment, the process 100 includes water splitting, for example, as is illustrated in Table 1, using cobalt oxide as the metal oxide 103 for producing the thermally-reduced metal oxide 105, to reduce the oxygenated-hydrocarbon 107, specifically methanol. In this embodiment, the process 100 includes reactions in a four-step metal oxide-methane cycle in which producing a fuel (step 106), such as the hydrogen 115, in part, synthesizes the methanol (step 108) that is fed back to the reducing (step 104).

TABLE 1

| Step | Reaction | ΔH, kcal @25° C. | Temperature, ° C. |
|---|---|---|---|
| 102 | $Co_3O_4 \rightarrow 3CoO + 1/2O_2$ | 46.89 | >800° C. |
| 104 | $3CoO + CH_3OH \rightarrow Co_3O_4 + CH_4$ | −16.68 | <300° C. |
| 106 | $H_2O + CH_4 \rightarrow CO + 3H_2$ | 49.21 | >800° C. |
| 108 | $CO + 2H_2 \rightarrow CH_3OH$ | −21.62 | 200-300° C. |
| Net | $H_2O \rightarrow H_2 + 1/2O_2$ | 57.8 | |

In one embodiment of the process 100, the efficiency of performing the thermal reduction (step 102) at 900° C., the producing of the hydrogen 115 (step 106) at 800° C., the reducing of the oxygenated-hydrocarbon 107 (step 104) at 300° C., and the re-producing of the methanol (step 108) at 300° C. is 63.8%; assuming full recuperation of sensible heat from the reduced cobalt oxide and reformed syngas, and with no heat recuperation the cycle efficiency is 46.9%.

TABLE 2

| Step | Reaction | ΔH, kcal @25° C. | Temperature, ° C. |
|---|---|---|---|
| 102 | $Co_3O_4 \rightarrow 3CoO + 1/2O_2$ | 46.89 | >800° C. |
| 104 | $3CoO + CH_3OH \rightarrow Co_3O_4 + CH_4$ | −16.68 | <300° C. |
| 106 | $CO_2 + CH_4 \rightarrow 2CO + 2H_2$ | 59.04 | >800° C. |
| 108 | $CO + 2H_2 \rightarrow CH_3OH$ | −21.62 | 200-300° C. |
| Net | $CO_2 \rightarrow CO + 1/2O_2$ | 67.63 | |

In one embodiment, the process 100 includes the oxygenated-hydrocarbon 107, specifically the methanol, being a product, such as, a product fuel as is shown in Table 3 and FIG. 1. In this embodiment, the carbon dioxide 119 and the water 117 are reformed in the presence of methane to produce syngas, which is then used to synthesize methanol 107.

TABLE 3

| Step | Reaction | ΔH, kcal @25° C. | Temperature, ° C. |
|---|---|---|---|
| 102 | $3Co_3O_4 \rightarrow 9CoO + 3/2O_2$ | 140.67 | >800° C. |
| 104 | $9CoO + 3CH_3OH \rightarrow 3Co_3O_4 + 3CH_4$ | −50.04 | <300° C. |
| 106 | $CO_2 + 2H_2O + 3CH_4 \rightarrow 4CO + 8H_2$ | 157.46 | >800° C. |
| 108 | $4CO + 8H_2 \rightarrow 4CH_3OH$ | −86.48 | 200-300° C. |
| Net | $CO_2 + 2H_2O \rightarrow CH_3OH + 3/2O_2$ | 161.61 | |

The embodiments of the process 100 described in Tables 1-3 show that by adjusting the relative amounts of the carbon dioxide 119 and the water 117 fed in the producing of the carbon monoxide 113 and the hydrogen 115 (step 106), syngas is capable of being produced with any ratio of the carbon monoxide 113 to the hydrogen 115. In one embodiment, some heat for the producing of the hydrogen 115 (step 106) or the thermally-reducing of the metal oxide 103 (step 102) is partially provided from the reducing of the oxygenated-hydrocarbon 107 (step 104) and/or the re-producing of the methanol (step 108).

According to embodiments of the process 100, all of the products and intermediate reactants shown in Tables 1-3 are readily separable. Oxygen gas produced in the thermally-reducing of the metal oxide 103 (step 102) is capable of being separated from the thermally-reduced metal oxide 105.

In one embodiment, the cobalt oxide reduction reaction in the thermally-reducing of the metal oxide 103 (step 102) is performed in air at temperatures down to about 940° C. In another embodiment, the temperature is lowered to about 800° C. by using an inert gas, such as nitrogen, argon, steam, or a combination thereof. These temperatures enable the use of heat pipes and packed-bed reactors constructed from conventional metals, in addition to other high-temperature materials.

The methane 109 produced in the reducing of the oxygenated-hydrocarbon 107 (step 104) is capable of being separated. In one embodiment, the reducing of the oxygenated-hydrocarbon 107 (step 104) is performed with the oxygenated-hydrocarbon 107 in the gas phase and any of the oxygenated-hydrocarbon 107 carried over being separated from the methane 109 by condensation.

The reducing of the oxygenated-hydrocarbon 107 (step 104) is performed at a thermodynamically favorable temperature, for example, less than about 380° C., for the reaction $3CoO+CH_3OH(g) \rightarrow CH_4(g)+Co_3O_4$. This embodiment is susceptible to side reactions resulting in the formation of the water 117 or the carbon dioxide 119, instead of the methane 109. In one embodiment, the reducing of the oxygenated-hydrocarbon 107 (step 104) is performed with few or without any side reactions, for example, by performing the reducing of the oxygenated-hydrocarbon 107 (step 104) at as low a temperature as possible and/or by using a catalyst (not shown) such as nickel, platinum, rhodium, copper, palladium, other suitable catalysts, or a combination thereof.

In one embodiment, the process 100 includes photochemical stimulation to the reducing of the oxygenated-hydrocarbon 107 (step 104), for example, as $CH_3OH+hv \rightarrow CH_4+\frac{1}{2}O_2$. Because the oxygen binding energy in the oxygenated-hydrocarbon 107 is significantly less than for the water 117 or the carbon dioxide 119, a much higher fraction of the solar spectrum is capable of directly reducing methanol 107 to the methane 109, than for the water 117 or the carbon dioxide 119 photolysis reactions, thereby permitting an embodiment with the thermally-reducing of the metal oxide 103 (step 102) and the reducing of the oxygenated-hydrocarbon 107 (step 104) being combined.

In one embodiment, the reducing of the oxygenated-hydrocarbon 107 (step 104) is in a single syngas reduction step in the process 100, as is shown in the three-step embodiment depicted in FIG. 2. FIG. 2 specifically shows a carbon dioxide splitting three-step cycle corresponding to Table 4. For water splitting, the reducing of the oxygenated-hydrocarbon 107 (step 104) proceeds according to the following reaction, $3CoO+CO+2H_2 \rightarrow Co_3O_4+CH_4$, as part of a three-step metal oxide-methane cycle with the hydrogen 115 produced, for example, as a product fuel.

TABLE 4

| Step | Reaction | ΔH, kcal @25° C. | Temperature, ° C. |
|---|---|---|---|
| 102 | $Co_3O_4 \rightarrow 3CoO + 1/2O_2$ | 46.89 | >800° C. |
| 104 | $3CoO + CO_2 + 3H_2 \rightarrow Co_3O_4 + CH_4 + H_2O$ | −28.47 | <300° C. |
| 106 | $CH_4 + H_2O \rightarrow CO + 3H_2$ | 49.21 | >800° C. |
| Net | $CO_2 \rightarrow CO + 1/2O_2$ | 67.63 | |

The re-oxidation of the reduced metal oxide using syngas 115 (step 104) for hydrogen production is thermodynamically favorable with products and reactants at their standard state at temperatures less than about 300° C. However, because the reaction results in fewer moles in the gas phase, increasing reaction pressure improves the reaction potential and increases the temperature range in a manner similar to conventional methanol synthesis.

The process 100 includes any suitable additional steps. In one embodiment, the process 100 includes producing a synthesized oxygenated-hydrocarbon from at least a portion of the carbon monoxide 113 and the hydrogen 115. In a further embodiment, the process 100 includes using the synthesized oxygenated-hydrocarbon as the oxygenated-hydrocarbon 107 for further reduction. Additionally or alternatively, in one embodiment, the process 100 includes using the re-oxidized metal oxide 103 for further thermal reduction and/or further cycles.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A thermochemical process, comprising:
   reducing an oxygenated-hydrocarbon with reduced metal oxide to form an alkane; and
   using the alkane in a reforming reaction as a reducing agent for water, a reducing agent for carbon dioxide, or a combination thereof;
   wherein the process is devoid of metal sulfate.

2. The process of claim 1, wherein the reducing of the oxygenated-hydrocarbon produces a re-oxidized metal oxide.

3. The process of claim 1, further comprising producing carbon monoxide and hydrogen from the alkane, the water, the carbon dioxide, or a combination thereof.

4. The process of claim 3, further comprising producing a synthesized oxygenated-hydrocarbon from at least a portion of the carbon monoxide and the hydrogen.

5. The process of claim 4, further comprising using the synthesized oxygenated-hydrocarbon for further re-oxidation a reduced metal oxide.

6. The process of claim 3, wherein the producing of the carbon monoxide and the hydrogen is at a temperature of less than 1000° C.

7. The process of claim 3, wherein the producing of the carbon monoxide or the hydrogen is at a temperature of less than 1000° C.

8. The process of claim 1, wherein the process is devoid of $SO_2$.

9. The process of claim 1, wherein the process is devoid of dopants.

10. The process of claim 1, wherein the process is devoid of catalysts.

11. The process of claim 1, wherein the process includes at least three steps.

12. The process of claim 1, wherein the process includes at least four steps.

13. The process of claim 1, further comprising promoting splitting of one or both of the water and the carbon dioxide by one or both of photochemical and electrochemical stimulus.

14. The process of claim 13, wherein the promoting of the splitting is at a temperature of less than 1000° C.

15. The process of claim 1, wherein the alkane is methane.

16. The process of claim 1, wherein the process produces fuel.

17. The process of claim 1, wherein the fuel is hydrogen, carbon monoxide, syngas, methanol, ethanol, butanol, propanol, or a combination thereof.

18. A thermochemical process, comprising:
reducing a metal oxide to form a reduced metal oxide;
reducing an oxygenated-hydrocarbon with the reduced metal oxide to form an alkane; and
using the alkane in a reforming reaction as a reducing agent for water, a reducing agent for carbon dioxide, or a combination thereof.

* * * * *